United States Patent [19]
Blok et al.

[11] Patent Number: 5,981,637
[45] Date of Patent: Nov. 9, 1999

[54] RUBBER COMPOSITION WHICH CONTAINS ANTI-REVERSION MATERIAL AND TIRE WITH COMPONENT THEREOF

[75] Inventors: Edward John Blok, Wadsworth; Lawson Gibson Wideman, Hudson; Paul Harry Sandstrom, Tallmadge; John Eugene Varner, Barberton, all of Ohio

[73] Assignee: The Goodyear Tire & Rubber Company, Akron, Ohio

[21] Appl. No.: 09/135,144

[22] Filed: Aug. 17, 1998

[51] Int. Cl.⁶ ........................................ C08K 5/20
[52] U.S. Cl. ........................ 524/219; 524/210; 524/217; 524/218; 525/332.7
[58] Field of Search ..................... 524/210, 217, 524/218, 219; 525/332.7

[56] References Cited

U.S. PATENT DOCUMENTS

| | | | |
|---|---|---|---|
| 5,610,240 | 3/1997 | Hogt et al. | 525/332.6 |
| 5,623,007 | 4/1997 | Kebler | 524/105 |
| 5,698,620 | 12/1997 | Wideman et al. | 524/270 |
| 5,844,049 | 12/1998 | Dotta et al. | 525/332.6 |

*Primary Examiner*—Edward J. Cain
*Attorney, Agent, or Firm*—Henry C Young, Jr.

[57] ABSTRACT

The invention relates to a rubber composition which contains a tris (maleamic acid derivative)amine as an anti-reversion additive. The invention also relates to a tire having a component of such rubber composition.

43 Claims, No Drawings

RUBBER COMPOSITION WHICH CONTAINS ANTI-REVERSION MATERIAL AND TIRE WITH COMPONENT THEREOF

FIELD

The invention relates to a rubber composition which contains a tris (maleamic acid derivative)amine as an anti-reversion additive and to a tire having a component of such rubber composition.

BACKGROUND

Rubber compositions are typically used for tire treads which may be optimized for various rubber composition properties to promote three tire properties; namely, traction, rolling resistance and treadwear.

In this regard, typically desirable physical properties for tire tread rubber compositions may include, for example, hardness, modulus, hysteresis as indicated by rebound properties, tangent delta (Tan. delta) at 0° C., and abrasion resistance as indicated by DIN abrasion values. Such physical properties are well known to those having skill in the rubber compounding art and, in general, are considered to be predictive of tire tread performance.

The phenomenon of reversion in the accelerated sulfur vulcanization of cis 1,4-polyisoprene (natural or synthetic) or other diene-based elastomers is undesirable. Reversion occurs when polysulfidic crosslinks deteriorate with time and temperature. Subsequently, this leads to a reduction in crosslink density and a deterioration of physical properties (lower modulus and higher hysteresis).

Accordingly, it remains desirable to utilize a reversion resistant additive in various rubber compositions.

In the description of this invention, the term "phr," where used herein, and according to conventional practice, refers to "parts of a respective material per 100 parts by weight of rubber or elastomer".

In the description of this invention, the terms "rubber" and "elastomer," if used herein, may be used interchangeably, unless otherwise prescribed. The terms "rubber composition," "compounded rubber" and "rubber compound," if used herein, are used interchangeably to refer to "rubber which has been blended or mixed with various ingredients and materials" and such terms are well known to those having skill in the rubber mixing or rubber compounding art.

SUMMARY AND DESCRIPTION OF THE INVENTION

In accordance with this invention, a rubber composition is provided which comprises (A) 100 parts by weight of at least one diene-based elastomer and (B) about 0.5 to about 10 phr of a tris(maleamic acid derivative)amine of the following formula I:

(I)

wherein the alkylene radical is a saturated hydrocarbon radical containing from one to 12, preferably from 1 to 4 carbon atoms, which may be linear or branched; R' and R" may be the same or different radicals selected from hydrogen, alkyl radicals having from 1 to 6 carbon atoms, and halo radicals.

Preferably said alkylene radical is selected from the group consisting of methylene, ethylene, propylene, butylene or pentylene radicals.

Preferably, R' and R" radicals are selected from hydrogen, methyl, chloro and bromo radicals.

More preferably R' and R" are selected rom hydrogen and methyl radicals.

Representative examples of tris (maleamic acid derivative) amines for this invention are, for example, adducts formed by reacting tris(2-aminoethyl)amine and maleic or citraconic anhydride to provide the corresponding tris(maleamic acid derivative)amine. Such adducts might be, for example, tris(citraconamic acid methyl) amine, tris (maleamic acid ethyl) amine, tris(citraconamic acid propyl) amine and the like.

A more preferred tris (maleamic acid derivative) amine is tris(2-citraconamic acid ethyl) amine.

In further accordance with this invention, a tire having a component, particularly a tread, of such rubber composition is provided.

FURTHER DETAILED DESCRIPTION

It is considered that this invention is particularly applicable where it is desired to endeavor to minimize reversion in rubber composition applications where such compositions are to be subjected to relatively high temperature use under dynamic working conditions. Such reversion may be evidenced by dynamic aging of various physical properties of the rubber composition usually resulting in a reduction of one or more desirable physical property values for the rubber composition such as, for example, modulus, rebound and/or hardness values.

The tris (maleamic acid derivative)amine for use in this invention, while its mechanism may not be completely understood, is believed to be an elastomer and filler interactive material in a manner to resist reversion of elastomer composition properties at elevated temperatures under dynamic working conditions.

In general, it is considered herein that a tris (maleamic acid derivative) amine may be synthesized, for example, by combining a tris(aminoalkyl)amine with an acid anhydride under suitable reaction conditions.

In this invention, the tris (maleamic acid derivative) amine has been observed to act somewhat as a rubber chemical which controls, or inhibits, reversion of rubber composition properties under conditions of elevated temperatures and dynamic conditions. This is considered herein to be particularly beneficial for rubber tire applications where heat build-up, and accompanying elevated temperatures under dynamic working conditions are present.

In the practice of this invention, as hereinbefore pointed out, the rubber composition is comprised of at least one diene-based elastomer, or rubber. Such elastomers are typically selected from homopolymers and copolymers of conjugated dienes and copolymers of conjugated diene(s) and vinyl aromatic monomers such as, for example, styrene and alpha-methylstyrene. Such dienes may, for example, be selected from isoprene and 1,3-butadiene and such vinyl aromatic monomers may be selected from styrene and alpha-methylstyrene. Such elastomer, or rubber, may be selected, for example, from at least one of cis 1,4-polyisoprene rubber (natural and/or synthetic, and preferably natural rubber), 3,4-polyisoprene rubber, styrene/butadiene copolymer rubbers, isoprene/butadiene copolymer rubbers, styrene/isoprene copolymer rubbers, styrene/isoprene/butadiene terpolymer rubbers, cis 1,4- polybutadiene rubber, trans 1,4-polybutadiene rubber (70–95 percent trans), low vinyl polybutadiene rubber (10–30 percent vinyl), high vinyl polybutadiene rubber (30–90 percent vinyl).

In one aspect, the rubber is preferably comprised of at least two diene-based rubbers. For example, a combination of two or more rubbers is preferred such as cis 1,4-polyisoprene rubber (natural or synthetic, although natural is usually preferred), 3,4-polyisoprene rubber, isoprene/butadiene copolymer rubber, styrene/isoprene/butadiene rubber, emulsion and solution polymerization derived styrene/butadiene rubbers, cis 1,4-polybutadiene rubbers, medium vinyl polybutadiene rubbers (30–55 percent vinyl), high vinyl polybutadiene rubbers (55–90 percent vinyl) and emulsion polymerization prepared butadiene/acrylonitrile copolymers.

Such elastomers are intended to include tin-coupled and/or silica-coupled end functionalized organic solution polymerization prepared elastomers (ie: for example, amine and hydroxyl end functionalized elastomers) and, also lithium produced solution polymerization prepared elastomers containing units derived from isoprene, 1,3-butadiene and styrene which have been coupled with tin tetrachloride or silicon tetrachloride.

It is readily understood by those having skill in the art that the rubber composition would be compounded by methods generally known in the rubber compounding art, such as mixing the various sulfur-vulcanizable constituent rubbers with various commonly used additive materials such as, for example, curing aids, such as sulfur, activators, retarders and accelerators, processing additives, such as oils, resins including tackifying resins, coupling agent, and plasticizers, fillers, pigments, fatty acid, zinc oxide, waxes, antioxidants and antiozonants, peptizing agents and reinforcing materials such as, for example, carbon black. As known to those skilled in the art, depending on the intended use of the sulfur-vulcanizable and sulfur-vulcanized material (rubbers), the additives mentioned above are selected and commonly used in conventional amounts.

The composition of the present invention may contain conventional amounts of known rubber chemicals.

Typical amounts of tackifier resins, if used, may comprise about 0.5 to about 10 phr, usually about 1 to about 5 phr. Typical amounts of processing aids comprise about 1 to about 50 phr. Such processing aids can include, for example, aromatic, napthenic, and/or paraffinic processing oils. Typical amounts of antioxidants comprise about 1 to about 5 phr. Representative antioxidants may be, for example, diphenyl-p-phenylenediamine and others such as, for example, those disclosed in *The Vanderbilt Rubber Handbook* (1978), pages 344–346. Typical amounts of antiozonants comprise about 1 to 5 phr. Typical amounts of fatty acids, if used, which are usually comprised primarily of stearic acid, comprise about 0.5 to about 3 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

The vulcanization of the rubber composition is conducted in the presence of a sulfur-vulcanizing agent. Examples of suitable sulfur-vulcanizing agents include elemental sulfur (free sulfur) or sulfur-donating vulcanizing agents, for example, an amine disulfide, polymeric polysulfide or sulfur olefin adducts. Preferably, the sulfur-vulcanizing agent is elemental sulfur. As known to those skilled in the art, sulfur-vulcanizing agents are used in an amount ranging from about 0.5 to about 4 phr, or even, in some circumstances, up to about 8 phr, with a range of from about 1.5 to about 2.5, sometimes from about 2 to about 2.5, being preferred.

Accelerators are used to control the time and/or temperature required for vulcanization and to improve the properties of the vulcanizate. In one embodiment, a single accelerator system may be used, i.e., primary accelerator. Conventionally and preferably, a primary accelerator(s) is used in total amounts ranging from about 0.5 to about 4, preferably about 0.8 to about 2, phr. In another embodiment, combinations of a primary and a secondary accelerator might be used with the secondary accelerator being used in amounts of about 0.05 to about 5 phr in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

The presence and relative amounts of most of the above additives are not considered to be an aspect of the present invention which is more primarily directed to the utilization of the aforesaid anti-reversion compound.

The rubber composition may be and is preferably prepared by mixing the diene-based rubber, carbon blacks and other rubber compounding ingredients, exclusive of the rubber curatives, in at least one sequential mixing step with at least one mechanical mixer, usually referred to as "non-productive" mix stage(s), to a temperature in a range of about 150° C. to about 180° for one to about 4 minutes, followed by a final mix stage in which the curatives, such as sulfur and accelerators, are added and mixed therewith for about 1 to about 4 minutes to a temperature within a range of about 90° C. to about 125° C. The terms "non-productive" and "productive" mix stages are well known to those having skill in the rubber mixing art.

It is to be appreciated that the rubber composition is conventionally cooled to a temperature below about 40° C. between the aforesaid mix stages.

It is to be further appreciated that the aforesaid duration of time for the required temperature maintenance for the mixing process(es) during the non-productive mix stages can be accomplished, for example, by (i) adjusting the motor speed of the mixer, namely reducing the motor speed after the desired temperature of the rubber composition is reached, in a variable speed mixer or by (ii) utilizing two or more mix stages sufficient to satisfy the duration requirement for the aforesaid maximum mixing temperature maintenance.

Vulcanization of the rubber composition of the present invention is generally carried out at conventional temperatures ranging from 100° C. to 200° C. Preferably, the vulcanization is conducted at temperatures ranging from 110° C. to 180° C. Any of the usual vulcanization processes may be used such as heating in a press or mold, heating with superheated steam or hot air or in a salt bath.

Upon vulcanization of the sulfur-vulcanized composition, the rubber composition of this invention can be used for various purposes. For example, the sulfur-vulcanized rubber composition may be in the form of a tread for a pneumatic tire which is the subject of this invention. Such tires can be built, shaped, molded and cured by various methods which are known and will be readily apparent to those having skill in such art. As can be appreciated, the tire may be a passenger tire, aircraft tire, truck tire and the like. Preferably, the tire is a passenger tire. The tire may also be radial or bias, with a radial tire being preferred.

The invention may be better understood by reference to the following examples in which the parts and percentages are by weight unless otherwise indicated.

EXAMPLE I

A round bottom 3-liter flask was swept with nitrogen and charged with 49 g (0.34 mole) of tris(2-aminoethyl)amine in 1500 ml of reagent acetone. The solution was stirred as 112 g (1.01 mole) of citraconic anhydride in 500 ml of reagent acetone was added in a dropwise fashion over about 1½ hours and the exothermic nature of the reaction was allowed to heat the reaction mixture as additional heat was added to cause it to reflux.

The reflux was continued for about 3 hours and the acetone was distilled away under a reduced pressure of about 29 inches of mercury at about 50° C. to yield about 166 grams of a dark amber semi-solid which was shown by NMR analysis in $CDCl_3$ to be the tris citraconamic acid derivative. One hundred grams of the semi-solid was dissolved in 100 g of reagent acetone and added to 100 g of N330 carbon black while stirring the mixture. The acetone was removed at about 50° C. under about 29 inches of Hg vacuum to yield black friable granules of tris(2-citraconamic acid ethyl)amine on carbon black in a weight ratio of about 1/1.

EXAMPLE II

In this example, rubber compositions are prepared which contain a tris (maleamic acid derivative) amine prepared by Example I. The rubber compositions are referred to herein as the Control (Cntrl) and Exp A.

All of the rubber compositions for this Example were prepared as a blend of emulsion polymerization prepared styrene/butadiene copolymer rubber, and cis 1,4-polybutadiene rubber.

The compositions were prepared by mixing the ingredients in several stages, namely, one non-productive stage (without the curatives) followed by a productive mix stage (for the curatives), then the resulting composition was cured under conditions of elevated pressure and temperature.

For the non-productive mixing stage, exclusive of the accelerator(s) and sulfur curatives which are mixed (added) in the final, productive mixing stage, the ingredients, including the elastomers, are mixed for about four minutes to a temperature of about 160° C. In a final productive mixing stage the curatives are mixed with the rubber composition (mixture) in a Banbury type mixer; namely, the accelerator (s) and sulfur to a maximum temperature of about 110° C. for about three minutes.

The resulting rubber compositions were then vulcanized at a temperature of about 150° C. for about 18 minutes.

The following Table 1 relates to the ingredients used for the Control and Exp. A formulations.

TABLE 1

| Sample No. | Cntrl | Exp A |
|---|---|---|
| Non-Productive Mix Stage | | |
| E-SBR Rubber[1] | 70 | 70 |
| Cis BR Rubber[2] | 30 | 30 |
| Processing Oil/Aids[3] | 47.55 | 47.55 |
| Zinc Oxide | 2 | 2 |
| Fatty Acid | 2 | 2 |
| Antioxidant[4] | 1.15 | 1.15 |
| Carbon Black (N299)[5] | 70 | 70 |
| Tris amine[6] | 0 | 3 |
| Productive Mix Stage | | |
| Sulfur | 1.45 | 1.45 |
| Accelerators[7] | 1.50 | 1.50 |

[1]Emulsion polymerization prepared styrene/butadiene copolymer rubber obtained as PLF 1712 from The Goodyear Tire & Rubber Company having a styrene content of about 23.5 percent and a Tg of about −55° C.;
[2]Cis 1,4-polybutadiene rubber obtained as BUDENE ® 1254 a trademark of The Goodyear Tire & Rubber Company having a cis content of about 98 percent; also contains 25 phr aromatic oil;
[3]Aromatic rubber processing oil, wax, etc.;
[4]Of the alkylaryl paraphenylene diamine type;
[5]ISAF carbon black having an Iodine Number of about 122 g/kg and a corresponding DBP Adsorption Number of about 114 cc/100 gm;
[6]a tris (maleamic acid derivative) amine from Example I herein;
[7]Accelerators of the sulfenamide type.

The physical properties for the resulting vulcanized rubber compositions are shown in the following Table 2.

The various tests are considered herein to be well known to those having skill in such analytical art. A description of the anti-reversion test may be found in U.S. Pat. No. 5,736,611.

TABLE 2

| Sample No. | Control | Exp. A |
|---|---|---|
| Break-Strength, MPa | 17.1 | 14.4 |
| Elongation @ Break, % | 653 | 663 |
| 300% Modulus, MPa | 5.75 | 4.79 |
| Hardness, RT | 60.7 | 62.1 |
| Hardness, 100° C. | 49 | 48.4 |
| Rebound, RT | 32.1 | 30.9 |
| Rebound, 100° C. | 48.1 | 44.6 |
| Rheometer 191° C. | | |
| ML, dNm | 7 | 7 |
| MHR, dNm | 26.3 | 25 |
| delta M | 19.3 | 18 |
| $T_{25}$ | 1.5 | 1.5 |
| $T_{90}$ | 2.25 | 2 |
| Reversion (time to decrease designated points below maximum torque of compound) | | |
| Max Torque − 1 dNm (min.) | 1.25 | 3.25 |
| Max Torque − 2 dNm (min.) | 3.75 | none |
| Marching Modulus (Time to rise after maximum reversion) | | |
| Max Torque + 1 dNm (min.) | none | 12.5 |
| Max Torque + 2 dNm (min.) | none | 23 |

The addition of amine additive demonstrated a significant improvement in the high temperature stability of the Exp A compound. The rheometer curve at 191° C. showed a significant reduction in reversion for the Exp A compound. The Exp A compound also showed a marching modulus which was not observed for the control. This would suggest that even higher temperatures of cure could be tolerated with the experimental compound without appreciable reversion taking place.

Therefore, it is considered herein that a particular benefit of using the amine is the high temperature stability it imparts to sulfur cured rubber compositions.

While certain representative embodiments and details have been shown for the purpose of illustrating the invention, it will be apparent to those skilled in this art that various changes and modifications may be made therein without departing from the spirit or scope of the invention.

What is claimed is:

1. In accordance with this invention, a rubber composition comprises (A) 100 parts by weight of at least one diene-based elastomer and (B) about 0.5 to about 10 phr of a tris(maleamic acid derivative)amine of the following formula I:

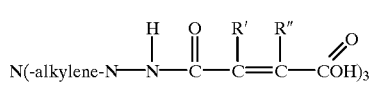
(I)

wherein the alkylene radical is a saturated linear or branched hydrocarbon radical containing from one to 12 carbon atoms; R' and R" are the same or different radicals selected from hydrogen, alkyl radicals having from one to 6 carbon atoms, and halo radicals.

2. The rubber composition of claim 1 wherein said diene-based elastomer is selected from homopolymers of 1,3-butadiene or isoprene, from copolymers of 1,3-butadiene and isoprene and from copolymers of at least one of 1,3-butadiene and isoprene with a vinyl aromatic monomer selected from styrene and alpha-methylstyrene.

3. The rubber composition of claim 2 wherein at least one of said diene-based elastomers is a tin or silicon coupled elastomer or an end functionalized elastomer.

4. The rubber composition of claim 1 wherein said alkylene radical is selected from the group consisting of methylene, ethylene, propylene, butylene and pentylene radicals.

5. The rubber composition of claim 1 wherein said alkylene radical contains from one to four carbon atoms and R' and R" are selected from hydrogen, methyl, chloro and bromo radicals.

6. The rubber composition of claim 4 wherein R' and R" are selected from hydrogen and methyl radicals.

7. The rubber composition of claim 5 wherein R' and R" are selected from hydrogen and methyl radicals.

8. The rubber composition of claim 2 wherein said alkylene radical is selected from the group consisting of methylene, ethylene, propylene, butylene and pentylene radicals.

9. The rubber composition of claim 2 wherein said alkylene radical contains from one to four carbon atoms and R' and R" are selected from hydrogen, methyl, chloro and bromo radicals.

10. The rubber composition of claim 8 wherein R' and R" are selected from hydrogen and methyl radicals.

11. The rubber composition of claim 9 wherein R' and R" are selected from hydrogen and methyl radicals.

12. The rubber composition of claim 3 wherein said alkylene radical is selected from the group consisting of methylene, ethylene, propylene, butylene and pentylene radicals.

13. The rubber composition of claim 3 wherein said alkylene radical contains from one to four carbon atoms and R' and R" are selected from hydrogen, methyl, chloro and bromo radicals.

14. The rubber composition of claim 12 wherein R' and R" are selected from hydrogen and methyl radicals.

15. The rubber composition of claim 13 wherein R' and R" are selected from hydrogen and methyl radicals.

16. The rubber composition of claim 1 wherein said tris(maleamic acid derivative)amine is a reaction product of a primary tris(aminoalkyl)amine with an acid anhydride.

17. The rubber composition of claim 1 wherein said tris(maleamic acid derivative)amine is a reaction product of tris(2-aminoethyl)amine and maleic or citraconic anhydride.

18. The rubber composition of claim 1 wherein said tris(maleamic acid derivative)amine is selected from at least one of the group consisting of tris(citraconamic acid methyl) amine, tris(maleamic acid ethyl) amine and tris (citraconamic acid propyl)amine.

19. The rubber composition of claim 2 wherein said tris(maleamic acid derivative)amine is selected from at least one of the group consisting of tris(citraconamic acid methyl) amine, tris(maleamic acid ethyl) amine and tris (citraconamic acid propyl)amine.

20. The rubber composition of claim 3 wherein said tris(maleamic acid derivative)amine is selected from at least one of the group consisting of tris(citraconamic acid methyl) amine, tris(maleamic acid ethyl)amine and tris(citraconamic acid propyl)amine.

21. A tire having a component of the rubber composition of claim 1.

22. A tire having a component of the rubber composition of claim 2.

23. A tire having a component of the rubber composition of claim 3.

24. The tire of claim 21 wherein said component is a tread.

25. The tire of claim 22 wherein said component is a tread.

26. The tire of claim 23 wherein said component is a tread.

27. A tire having a tread of the rubber composition of claim 4.

28. A tire having a tread of the rubber composition of claim 5.

29. A tire having a tread of the rubber composition of claim 6.

30. A tire having a tread of the rubber composition of claim 7.

31. A tire having a tread of the rubber composition of claim 8.

32. A tire having a tread of the rubber composition of claim 9.

33. A tire having a tread of the rubber composition of claim 10.

34. A tire having a tread of the rubber composition of claim 11.

35. A tire having a tread of the rubber composition of claim 12.

36. A tire having a tread of the rubber composition of claim 13.

37. A tire having a tread of the rubber composition of claim 14.

38. A tire having a tread of the rubber composition of claim 15.

39. A tire having a tread of the rubber composition of claim 16.

40. A tire having a tread of the rubber composition of claim 17.

41. A tire having a tread of the rubber composition of claim 18.

42. A tire having a tread of the rubber composition of claim 19.

43. A tire having a tread of the rubber composition of claim 20.

* * * * *